United States Patent
Fujii

(10) Patent No.: US 11,759,179 B2
(45) Date of Patent: Sep. 19, 2023

(54) ULTRASONIC DIAGNOSTIC APPARATUS AND CONTROL METHOD FOR ULTRASOUND IMAGE QUALITY ENHANCEMENT

(71) Applicant: FUJIFILM Healthcare Corporation, Kashiwa (JP)

(72) Inventor: Nobuhiko Fujii, Chiba (JP)

(73) Assignee: FUJIFILM Healthcare Corporation, Kashiwa (JP)

( * ) Notice: Subject to any disclaimer, the term of this patent is extended or adjusted under 35 U.S.C. 154(b) by 0 days.

(21) Appl. No.: 17/572,749

(22) Filed: Jan. 11, 2022

(65) Prior Publication Data
US 2022/0225965 A1    Jul. 21, 2022

(30) Foreign Application Priority Data

Jan. 18, 2021  (JP) ................. 2021-005441

(51) Int. Cl.
*A61B 8/00*      (2006.01)
*A61B 8/08*      (2006.01)
*G01S 15/89*     (2006.01)

(52) U.S. Cl.
CPC .......... *A61B 8/5207* (2013.01); *A61B 8/4494* (2013.01); *A61B 8/54* (2013.01); *G01S 15/8915* (2013.01)

(58) Field of Classification Search
CPC ....... A61B 8/5207; A61B 8/4494; A61B 8/54; G01S 15/8915
See application file for complete search history.

(56) References Cited

U.S. PATENT DOCUMENTS

| | | | |
|---|---|---|---|
| 5,301,674 A | 4/1994 | Erikson et al. | |
| 11,272,906 B2* | 3/2022 | Park | G01S 15/8927 |
| 2012/0041312 A1* | 2/2012 | Nakahira | G06T 5/50 |
| | | | 600/443 |
| 2014/0046187 A1 | 2/2014 | Taniguchi et al. | |
| 2016/0324505 A1* | 11/2016 | Maeda | A61B 8/5238 |
| 2020/0367862 A1 | 11/2020 | Taniguchi | |
| 2022/0128675 A1* | 4/2022 | Fatemi | G01S 15/8997 |

FOREIGN PATENT DOCUMENTS

| | | |
|---|---|---|
| JP | 2011-56249 A | 3/2011 |
| JP | 2018-153415 A | 10/2018 |

OTHER PUBLICATIONS

European search report dated Jul. 8, 2022 in corresponding European Patent Application No. 22150884.9.

* cited by examiner

*Primary Examiner* — Shahdeep Mohammed
*Assistant Examiner* — Amal Aly Farag
(74) *Attorney, Agent, or Firm* — Paul Teng

(57) ABSTRACT

A control unit cyclically sets a first transmission/reception condition for a close range and a second transmission/reception condition for a long range. A synthesizing unit generates an added frame sequence and an edge-enhanced frame sequence from a reception frame sequence, and generates a synthesized frame sequence from the added frame sequence and the edge-enhanced frame sequence. The first transmission/reception condition includes a first transmission frequency and a first transmission depth of focus. The second transmission/reception condition includes a second transmission frequency that is lower than the first transmission frequency and a second transmission depth of focus that is greater than the first transmission depth of focus.

7 Claims, 7 Drawing Sheets

ULTRASONIC DIAGNOSTIC APPARATUS AND CONTROL METHOD FOR ULTRASOUND IMAGE QUALITY ENHANCEMENT

CROSS REFERENCE TO RELATED APPLICATION

This application claims priority to Japanese Patent Application No. 2021-005441 filed on Jan. 18, 2021, which is incorporated herein by reference in its entirety including the specification, claims, drawings, and abstract.

TECHNICAL FIELD

The present disclosure relates to an ultrasonic diagnostic apparatus and a control method thereof, and particularly to a technique for improving quality of an ultrasound image.

BACKGROUND

Ultrasonic diagnostic apparatuses are medical apparatuses that form an ultrasound image based on received signals acquired by transmitting ultrasound waves into a living body (subject) and receiving ultrasound waves from within the living body. Specifically, ultrasound beams are electronically scanned repeatedly to generate a reception frame sequence composed of a plurality of reception frames (a plurality of reception frame data items) arranged on a time sequence basis. Based on the reception frame sequence, a display frame sequence composed of a plurality of display frames (a plurality of display frame data items) arranged on a time sequence basis is generated. The display frame sequence is displayed as a moving image.

To enhance the image quality of an ultrasound image, a known technique generates a synthesized frame for each frame set of the reception frame sequence. More specifically, a plurality of intermediate frames are generated based on each frame set, and the intermediate frames are then synthesized to produce a synthesized frame. To generate the intermediate frames, a summation method and an edge extraction method, for example, are known.

In the summation method, a plurality of frames forming a frame set are added together to generate an added frame. In the edge extraction method, edge components are extracted based on a plurality of frames forming a frame set, to generate an edge-enhanced frame.

In an ultrasonic diagnostic apparatus disclosed in JP 2018-153415 A (Document 1), an added frame and an edge-enhanced frame are generated as a plurality of intermediate frames from a plurality of frames forming a frame set, and the added frame and the edge-enhanced frame are subjected to weighted summation to generate a synthesized frame. In generating the edge-enhanced frame, a wavelet fusion method is used. The technique disclosed in Document 1 modifies blur that appears at the time of adding a plurality of frames by blending the edge components. JP 2011-56249 A (Document 2) also discloses a wavelet fusion method. However, neither Document 1 nor Document 2 discloses varying the transmission depth of focus within a frame set having the same range of diagnostic depth.

Other known techniques for enhancing the image quality of an ultrasound image include spatial compounding and frequency compounding. In these methods, a plurality of frames with different properties are synthesized to generate a synthesized frame.

SUMMARY

An embodiment of the disclosure is directed toward enhancing the image quality of an entire ultrasound image. Another embodiment of the disclosure is directed toward enhancing the image quality of an ultrasound image both in an area close to a probe (shallow region) and an area far from the probe (deep region).

In an aspect of the disclosure, an ultrasonic diagnostic apparatus includes a generating unit configured to generate a frame sequence by repeating generation of transmitting signals and processing of received signals according to a plurality of transmission/reception conditions that are set cyclically, and a synthesizing unit configured to generate a synthesized frame sequence from the frame sequence and configured to generate, for each of frame sets in the frame sequence, a synthesized frame based on a plurality of frames forming each frame set. The plurality of transmission/reception conditions comprise a first transmission/reception condition for a close range and a second transmission/reception condition for a long range. The first transmission/reception condition includes a first transmission frequency and a first transmission depth of focus, and the second transmission/reception condition includes a second transmission frequency that is lower than the first transmission frequency and a second transmission depth of focus that is greater than the first transmission depth of focus.

In accordance with another aspect, a method of controlling an ultrasonic diagnostic apparatus includes generating a frame sequence by repeating generation of transmitting signals and processing of received signals according to a plurality of transmission/reception conditions that are set cyclically; for each of frame sets in the frame sequence, generating a plurality of intermediate frames having different properties based on each frame set; for each of the frame sets, synthesizing the plurality of intermediate frames to generate a synthesized frame for forming an ultrasound image; calculating an evaluation value based on at least one of the plurality of intermediate frames; and changing a combination of a plurality of transmission frequencies included in the plurality of transmission/reception conditions based on the evaluation value.

BRIEF DESCRIPTION OF DRAWINGS

Embodiments of the present disclosure will be described based on the following figures, wherein.

DESCRIPTION OF EMBODIMENTS

Figure 1:
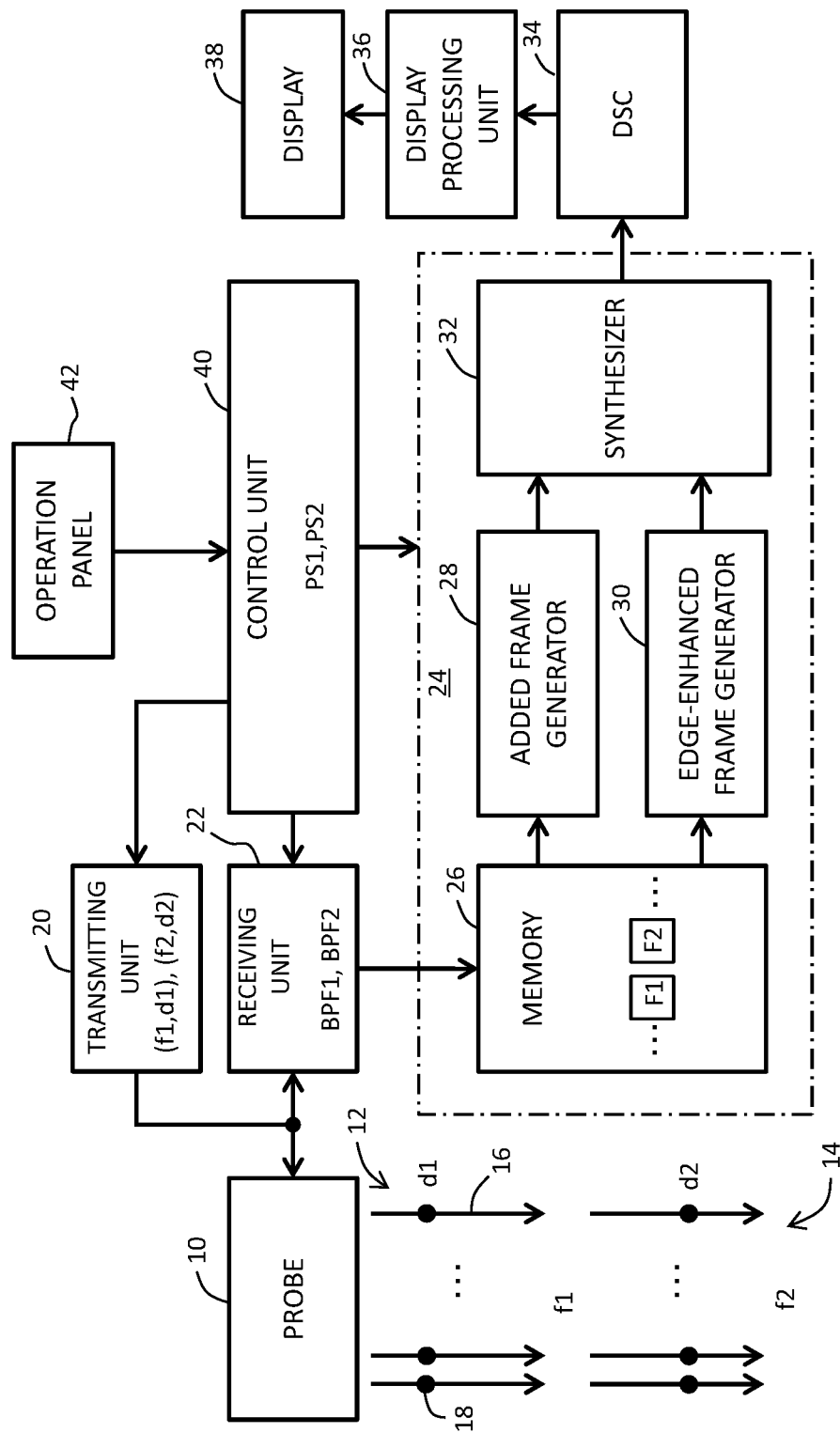
FIG. 1 is a block diagram illustrating a configuration of an ultrasonic diagnostic apparatus according to a first embodiment.

Embodiments of the disclosure will be described below by reference to the drawings.

(1) Summary of Embodiments

An ultrasonic diagnostic apparatus according to an embodiment includes a generating unit and a synthesizing unit. The generating unit repeats production of transmitting signals and processing of received signals according to a plurality of transmission/reception conditions that are cyclically established, thereby generating a frame sequence. The generating unit corresponds to a transmission/reception unit. The synthesizing unit generates a synthesized frame sequence from the frame sequence. More specifically, the synthesizing unit generates a synthesized frame for each of frame sets in the frame sequence based on a plurality of frames forming each frame set. The plurality of transmission/reception conditions include a first transmission/reception condition for a close range and a second transmission/reception condition for a long range. The first transmission/reception condition includes a first transmission frequency and a first transmission depth of focus, and the second transmission/reception condition includes a second transmission frequency that is lower than the first transmission frequency and a second transmission depth of focus that is greater than the first transmission depth of focus.

In the above configuration, a frame set is composed of a plurality of frames having different properties. These frames are synthesized to form a synthesized frame. In the process of creating each of the frame sets, there are selectively applied the first transmission/reception condition for a close range and the second transmission/reception condition for a long range, particularly a combination of the first transmission frequency and the first depth of focus and a combination of the transmission frequency and the second depth of focus. This configuration therefore enhances the image quality, particularly, the spatial resolution and sensitivity, of the synthesized frame generated by the synthesizing unit, both in a close range area and a long range area.

In an embodiment, in the process of applying a plurality of transmission/reception conditions stepwise, a range of diagnostic depth is maintained. This feature distinguishes the technique according to the embodiment from a conventional transmission multi-step focusing technique. Also, in the process of applying a plurality of transmission/reception conditions stepwise, a plurality of transmission depths of focus are set stepwise. This feature distinguishes the technique of the embodiment from the conventional frequency compounding method. The plurality of transmission/reception conditions include two transmission/reception conditions or three or more transmission/reception conditions. The frame sequence conceptually includes a reception frame sequence and a display frame sequence.

Typically, when the electronic linear scan method (including an electronic convex scan method) is employed, the transmission depth of focus is defined as a distance from a transmitting and receiving surface (normally a surface to be contact with a living body) of a probe in a direction orthogonal to the transmitting and receiving surface. When the electronic sector scanning method is employed, the transmission depth of focus is defined as a distance from a transmission/reception origin. The transmission frequency is typically a transmission center frequency.

The ultrasonic diagnostic apparatus according to an embodiment includes a control unit. The control unit determines the first transmission depth of focus and the second transmission depth of focus based on the range of diagnostic depth. This configuration enhances the image quality of an ultrasound image while reducing burden imposed on a user. To this end, a first ratio may be predetermined for the close range focus and a second ratio may be predetermined for a long range focus, for example. In this case, the transmission depth of focus for a close range is automatically determined by multiplying the first ratio by the range of diagnostic depth (the maximum depth for imaging). Similarly, the transmission depth of focus for a long range is automatically determined by multiplying the second ratio by the range of diagnostic depth.

In an embodiment, the first transmission/reception condition includes a first reception pass band, and the second transmission/reception condition includes a second reception pass band that is narrower than the first transmission pass band. Typically, a reception dynamic filter is used during a reception process. Specifically, a technique for dynamically varying the frequency pass band in accordance with a change in the reception depth of focus is employed. The first reception pass band and the second reception pass band are each a pass band at a predetermined depth, in a predetermined depth range, or in an entire depth range. For example, at the first transmission depth of focus and the second transmission depth of focus, the second reception pass band may be narrower than the first reception pass band.

In an embodiment, the first transmission/reception condition includes a first beam deflection angle, and the second transmission/reception condition includes a second beam deflection angle that differs from the first beam deflection angle. This configuration corresponds to a combination of the above-described configuration and the spatial compounding method.

The ultrasonic diagnostic apparatus according to an embodiment includes a transducer array including a plurality of transducers arranged in a main direction and a sub direction. The first transmission/reception condition includes a first aperture size that is an aperture size in the sub direction, and the second transmission/reception condition includes a second aperture size that is an aperture size in the sub direction and differs from the first aperture size.

In an embodiment, the synthesizing unit include a first synthesizing unit that generates a plurality of intermediate frames having different properties, based on a frame set, and a second synthesizing unit that synthesizes the plurality of intermediate frames to produce a synthesized frame. In an embodiment, the first synthesizing unit generates, as the plurality of intermediate frames, an added image and an edge-enhanced image, and the second synthesizing unit synthesizes the added image and the edge-enhanced image to generate a synthesized frame. This configuration uses the added image to enhance the sensitivity and uses the edge-enhanced image to increase the spatial resolution. In other words, this configuration enables modification of blur that appears in the added image by the blend of edge components.

The ultrasonic diagnostic apparatus according to an embodiment includes a calculating unit that calculates an evaluation value based on at least one of the plurality of intermediate frames, and a control unit that changes a combination of the first transmission frequency and the second transmission frequency based on the evaluation value. Properties of a subject, such as a quantity of fat, appear in the plurality of intermediate frames. The evaluation value indicative of the properties of the subject can be obtained by referencing some or all of the plurality of intermediate frames, and the combination of a plurality of transmission frequencies is changed or may be optimized in accordance with the evaluation value.

In an embodiment, the plurality of intermediate frames include the added image and the edge-enhance image. The evaluation value corresponds to a difference between the added image and the edge-enhanced image. The difference between the added image and the edge-enhanced image corresponds to an amount of edge, for example. When the amount of edge is small, the combination of the transmission frequencies is changed to increase the edge.

A control method for an ultrasonic diagnostic apparatus according to an embodiment includes a first step, a second step, a third step, a fourth step, and a fifth step. In the first step, generation of transmitting signals and processing of received signals are repeated according to a plurality of transmission/reception conditions cyclically established, to generate a frame sequence. In the second step, for each frame set in the frame sequence, a plurality of intermediate frames having different properties are generated based on each frame set. In the third step, for each frame set, the plurality of intermediate frames are synthesized to generate a synthesized frame for forming an ultrasound image. In the fourth step, an evaluation value is calculated based on at least one of the plurality of intermediate frames. In the fifth step, a combination of a plurality of transmission frequencies included in the plurality of transmission/reception conditions is changed based on the evaluation value.

The above configuration enhances the image quality of an ultrasound image. This configuration particularly enables feedback of information produced during the synthesizing processing to set the transmission/reception condition. For example, a relatively high transmission frequency pair is selected for a subject having less fat and a relatively low transmission frequency pair is selected for a subject having more fat.

In an embodiment, the plurality of intermediate frames include an added frame and an edge-enhanced frame. The evaluation value corresponds to a difference between the added frame and the edge-enhanced frame. The evaluation value may be calculated by integration of differences over the entire frame or within a partial frame. It may be the case that only the edge-enhanced frame is referenced.

(2) Details of Embodiments

FIG. 1 illustrates an ultrasonic diagnostic apparatus according to a first embodiment. A tissue to be diagnosed may be a liver, heart, or fetus, for example.

A probe 10 includes a probe head to be brought into contact with a living body. The probe head contains a transducer array composed of a plurality of transducers arranged one-dimensionally. The plurality of transducers are arranged linearly or in an arc shape. As will be described below, the probe head may contain a transducer array composed of a plurality of transducers arranged two-dimensionally.

In transmission, a transmitting unit 20 supplies a plurality of transmitting signals to the transducer array to allow emission of ultrasound waves into a living body. At this time, transmitting beams are formed. In reception, upon receiving reflection waves from within the living body, the transducer array outputs a plurality of received signals to a receiving unit 22. The receiving unit 22 applies, to the plurality of received signals, phase alignment and addition (delay and summing) to thereby generate received signals after the phase alignment and addition, which correspond to received beams.

An ultrasound beam corresponds to a beam generated by synthesizing the transmitting beam and the received beam. The ultrasound beams are electronically scanned. Electronic scanning methods include an electronic linear scan method (including an electronic convex scanning method), an electronic sector scanning method, and other methods. One electronic scan of an ultrasound beam produces one reception frame (one set of reception frame data). The reception frame is composed of a plurality of beam data items arranged in the electronic scanning direction. Each beam data item is composed of a plurality of echo data items arranged in the depth direction. Electronic scanning of the ultrasound beams is repeated to produce a plurality of reception frames arranged on a time sequence basis, which form a reception frame sequence. In FIG. 1, reference numeral 16 indicates an ultrasound beam (or a transmitting beam), and reference numeral 18 indicates a transmission focus.

The illustrated receiving unit 22 includes a plurality of A/D converters, a plurality of delay circuits, and a summation circuit, for example. The receiving unit 22 further includes a detection circuit and a logarithmic transformation circuit, for example. All or some of the functions of the receiving unit 22 are implemented by hardware or software. The transmitting unit 20 and the receiving unit 22 function as a generating unit that produces the reception frame sequence.

In an embodiment, a control unit 40 cyclically sets a plurality of transmission/reception conditions. In the first embodiment, the plurality of transmission/reception conditions include a first transmission/reception condition for a close range and a second transmission/reception condition for a long range. Specifically, the first transmission/reception condition is composed of a first parameter set PS1 and the second transmission/reception condition is composed of a second parameter set PS2. Each transmission/reception condition includes a transmission frequency, a transmission depth of focus, and a reception pass band (BPF that is used), for example. The two transmission/reception conditions are set alternately for each frame.

Specifically, the first transmission/reception condition includes a first transmission frequency f1, a first transmission depth of focus d1, and a first reception frequency band (BPF1), and the second transmission/reception condition includes a second transmission frequency f2, a second transmission depth of focus d2, and a second reception frequency band (BPF2). Here, a relationship $f1>f2$ and a relationship of $d1<d2$ are satisfied.

In reception, a reception dynamic filter method is applied. For example, at one or both of the transmission depths of focus d1 and d2, the pass band of the BPF2 is narrower than the pass band of the BPF1. The pass band of the BPF2 may be narrower than the pass band of the BPF1 over the entire range of diagnostic depth.

The transmission/reception condition that is suitable for imaging an area close to the probe 10 is set at the time of forming a first scan plane 12, and the second transmission/reception condition that is suitable for imaging an area far from the probe 10 is set at the time of forming a second scan plane 14. Cyclic setting of the first transmission/reception condition and the second transmission/reception condition enables alternate generation of the first scan plane 12 and the second scan plane 14. In other words, a first reception frame and a second reception frame having different properties can be obtained cyclically.

As described above, the control unit 40 controls cyclic setting of a plurality of transmission/reception conditions. Specifically, the control unit 40 provides to the transmitting unit the first transmission frequency f1 and the first transmission depth of focus d1, or the second transmission frequency f2 and the second transmission depth of focus d2. Similarly, the control unit 40 designates, with respect to the receiving unit 22, the first reception pass band (BPF1) for forming the first scan plane 12 and the second reception pass band (BPF2) for forming the second scan plane 14.

The range of diagnostic depth is identical for the first transmission/reception condition and the second transmission/reception condition. The range of diagnostic depth is designated by the user or is preset. In an embodiment, the control unit 40 automatically determines the first transmission depth of focus d1 and the second transmission depth of focus d2 in accordance with the range of diagnostic depth dmax, as will be described below.

The receiving unit 22 outputs the reception frame sequence. In the illustrated example configuration, the reception frame sequence is transmitted to a synthesizing unit 24 that is composed of a processor, for example. Alternatively, a processor forming the control unit 40, such as a CPU, may function as the synthesizing unit 24.

The synthesizing unit 24 generates a display frame sequence from the reception frame sequence. A memory 26 is composed of a semiconductor memory, for example, and has a ring buffer structure. The memory 26 may be two or three frame memories. The reception frame sequence is stored in the memory 26. The individual reception frames that are stored correspond to data after detection and also data before scan conversion. Synthesizing processing may be applied to an RF frame sequence before detection and a display frame sequence.

An added frame generator 28 and an edge-enhanced frame generator 30 function as an intermediate frame generating unit (a first synthesizing unit), and a synthesizer 32, which will be described below, functions as a second synthesizing unit. In the reception frame sequence, a reception frame set is defined for each of the individual reception frames. For example, a reception frame that is currently acquired and a reception frame that is immediately before the current reception frame form a reception frame set. A reception frame set is shifted along a time axis in unit of reception frames.

The added frame generator 28 adds up two reception frames forming a reception frame set, for each reception frame set, to generate an added frame. At this time, simple summation (averaging) and weighted summation (weighted averaging) are applied for each spatial address on the scan plane. The two reception frames that are added together apparently enhance the sensitivity. The above processing is applied for each reception frame set, thereby generating an added frame sequence from the reception frame sequence.

The edge-enhanced frame generator 30 applies a wavelet fusion method to two reception frames forming a reception frame set, for each reception frame set, to thereby generate an edge-enhanced frame. Specifically, wavelet transformation is applied to the two reception frames individually to thereby generate two transformed frames. The two transformed frames are fused to generate a fused frame. The fused frame is then subjected to inverse transformation (wavelet inverse transformation) to thereby generate an edge-enhanced frame. In fusing two transformed frames, a method for retaining or enhancing an edge component, such as a maximum value method, is employed.

The edge-enhanced frame may be generated using a method other than the wavelet fusion method, such as a difference method or an edge extraction filter method. However, use of the wavelet fusion method enables simple extraction of clear components while removing blur components. The edge-enhanced frame generator 30 generates an edge-enhanced frame sequence from the reception frame sequence.

The synthesizer 32 applies weighted summation to two intermediate frames; that is, the added frame and the edge-enhanced frame, to generate a synthesized frame. Specifically, the synthesizer 32 performs weighted summation for each address on the scan plane. A weighting factor pair to be used at this time is determined fixedly or dynamically. A high quality frame with its edge being enhanced or an edge-enhanced frame is generated by adding each edge-enhanced frame to each added frame. Blending the edge-enhanced frames enables an increase in the spatial resolution in the depth direction. The synthesizer 32 generates a synthesized frame sequence from the added frame sequence and the edge-enhanced frame sequence.

A digital scan converter (DSC) 34 generates a display frame sequence from the reception frame sequence (specifically, the synthesized frame sequence). The DSC 34 is composed of a processor. The DSC 34 may be implemented by a processor forming the control unit 40. The DSC 34 has a coordinate conversion function, a pixel interpolation function, a frame rate conversion function, and other functions. Individual display frames constituting the display frame sequence form a tomographic image, for example.

A display processing unit 36 has an image synthesizing function, a color calculation function, and other functions. The display frame sequence is transmitted via the display processing unit to a display 38, which displays an ultrasound image. Specifically, the display 38 displays a tomographic image in the form of a moving image.

The control unit 40 controls operations of the elements illustrated in FIG. 1. In an embodiment, the control unit 40 cyclically sets the transmission/reception conditions as described above. An operation panel 42 is connected with the control unit 40. The operation panel 42 includes a plurality of switches, a plurality of pinches, a trackball, and a keyboard, for example. The display 38 is an LCD or an inorganic EL display device, for example.

Figure 2:
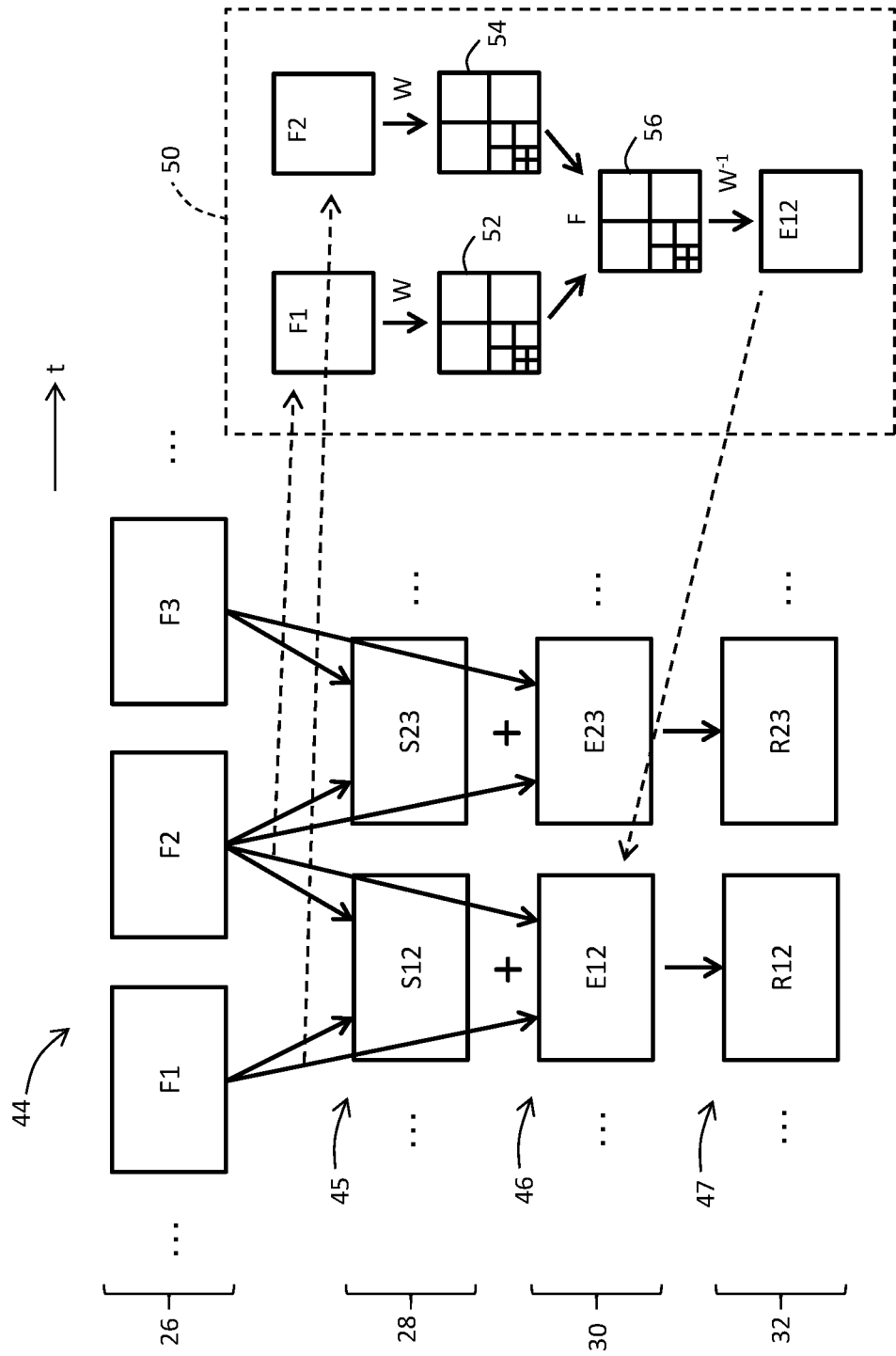
FIG. 2 schematically illustrates processing performed in a synthesizing unit.

FIG. 2 schematically illustrates processing performed by the synthesizing unit. The memory 26 temporarily stores a reception frame sequence 44. FIG. 2 illustrates reception frames F1, F2, and F3, among which the reception frame F3 is the newest. A frame set is formed for each reception frame. In the illustrated example, the reception frame F2 and the reception frame F3 form a reception frame set, and the reception frame F1 and the reception frame F2 form another reception frame set.

The added frame generator 28 adds up two reception frames forming each reception frame set to generate an added frame for each reception frame set. For example, the added frame generator 28 adds the reception frames F1 and F2 together to generate an added frame S12. The added frame generator 28 similarly adds the reception frames F2 and F3 together to generate an added frame S23. At this time, simple summation or weighted summation, for example, may be used. An added frame sequence 45 is generated from the reception frame sequence 44.

The edge-enhanced frame generator 30 applies the wavelet fusion method to two reception frames forming a reception frame set to generate an edge-enhanced frame for each reception frame set. For example, the edge-enhanced frame generator 30 generates an edge-enhanced frame E23 from the reception frames F2 and F3. The edge-enhanced frame generator 30 similarly generates an edge-enhanced frame E12 from the reception frames F1 and F2. An edge-enhanced frame sequence 46 is thus generated from the reception frame sequence 44.

The synthesizer 32 synthesizes the added frame and the edge-enhanced frame to generate a synthesized frame for each reception frame set. For example, the synthesizer 32 synthesizes the added frame S12 and the edge-enhanced frame E12 to generate a synthesized frame R12. The synthesizer 32 similarly synthesizes the added frame S23 and the edge-enhanced frame E23 to generate a synthesized frame R23. Consequently, a synthesized frame sequence 47 is generated from the reception frame sequence 44.

In an embodiment, a weight 0.8 is applied to the added frame and a weight 0.2 is applied to the edge-enhanced frame, for example. The relationship between the two weights may be dynamically changed in accordance with the situation.

FIG. 2 illustrates the content of the wavelet fusion method with reference numeral 50. The reception frames F1 and F2 are respectively subjected to wavelet transformation W, and transformed frames 52 and 54 are generated. The frames 52 and 54 are then fused to generate a fused frame 56, using the maximum value method, for example. The fused frame 56 is the subjected to inverse transformation $W^{-1}$ to thereby generate the edge-enhanced frame E12.

Figure 3:
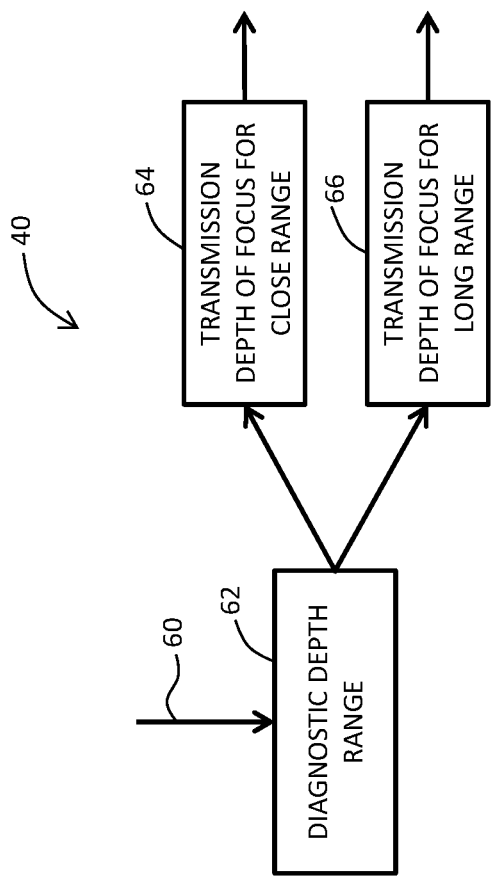
FIG. 3 illustrates a method of determining two depths of focus.

FIG. 3 illustrates a method of determining the transmission depth of focus. A range of diagnostic depth 62 is first determined by user designation 60, for example. The control unit 40 multiplies the range of diagnostic depth 62 by a first ratio to determine a transmission depth of focus 64 for a close range, and multiplies the range of diagnostic depth 62 by a second ratio to determine a transmission depth of focus 66 for a long range. The first ratio and the second ratio are previously determined or set by a user. The first ratio is ⅓ and the second ratio is ⅔, for example. The above processing enables automatic optimization of two transmission depths of focus. The two transmission depths of focus are displayed on the screen with two markers.

Figure 4:
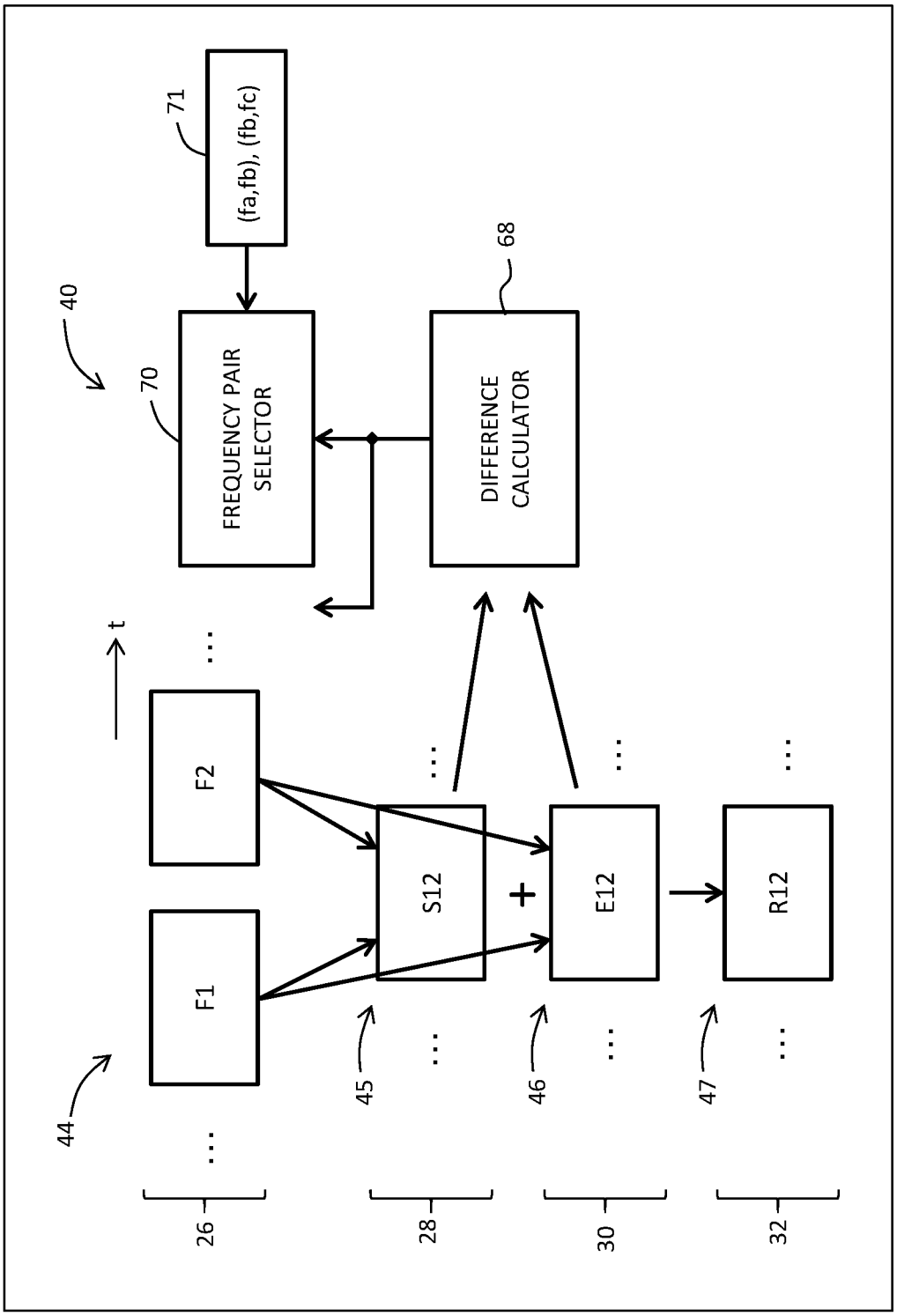
FIG. 4 illustrates a method of selecting frequency pairs.

FIG. 4 illustrates a method of selecting a frequency pair. Note that elements in FIG. 4 that are similar to elements shown in FIG. 2 are designated with the same reference numerals and will not be further described.

A difference calculator 68 calculates a difference between the added frame S12 and the edge-enhanced frame E12 generated from the same reception frame set. Specifically, a difference is calculated for each address on a scan plane (frame), and a sum of the differences is calculated for the entire frame. The sum is used as an evaluation value indicative of an edge amount.

A frequency pair selector 70 selects a specific transmission frequency pair from two transmission frequency pairs registered in a memory 71. In the illustrated example configuration, three transmission frequencies fa, fb, and fc are determined within a frequency band of the probe or within a range of frequencies that can be generated with the transmitting unit. These transmission frequencies fa, fb, and fc satisfy the relationship fa<fb<fc. For example, a transmission frequency pair (fb, fc) is first selected. Thereafter, in response to the calculated difference that is less than a predetermined threshold value; that is, in response to a small edge amount, another transmission frequency pair (fa, fb) is selected, because a subject has a great amount of fat and the transmission frequency needs to be lowered.

An optimum transmission frequency set may be selected in accordance with a difference, from among three or more transmission frequency sets that are previously provided. Other parameters, such as the reception pass band, may be changed in accordance with the difference. The difference may be calculated for each frame, or an average difference may be calculated within a predetermined time width. Transmission and reception may be repeated on a trial basis within a predetermined time period after start of the ultrasonic inspection so that the transmission frequency set may be automatically optimized based on a difference obtained within the time period.

Figure 5:
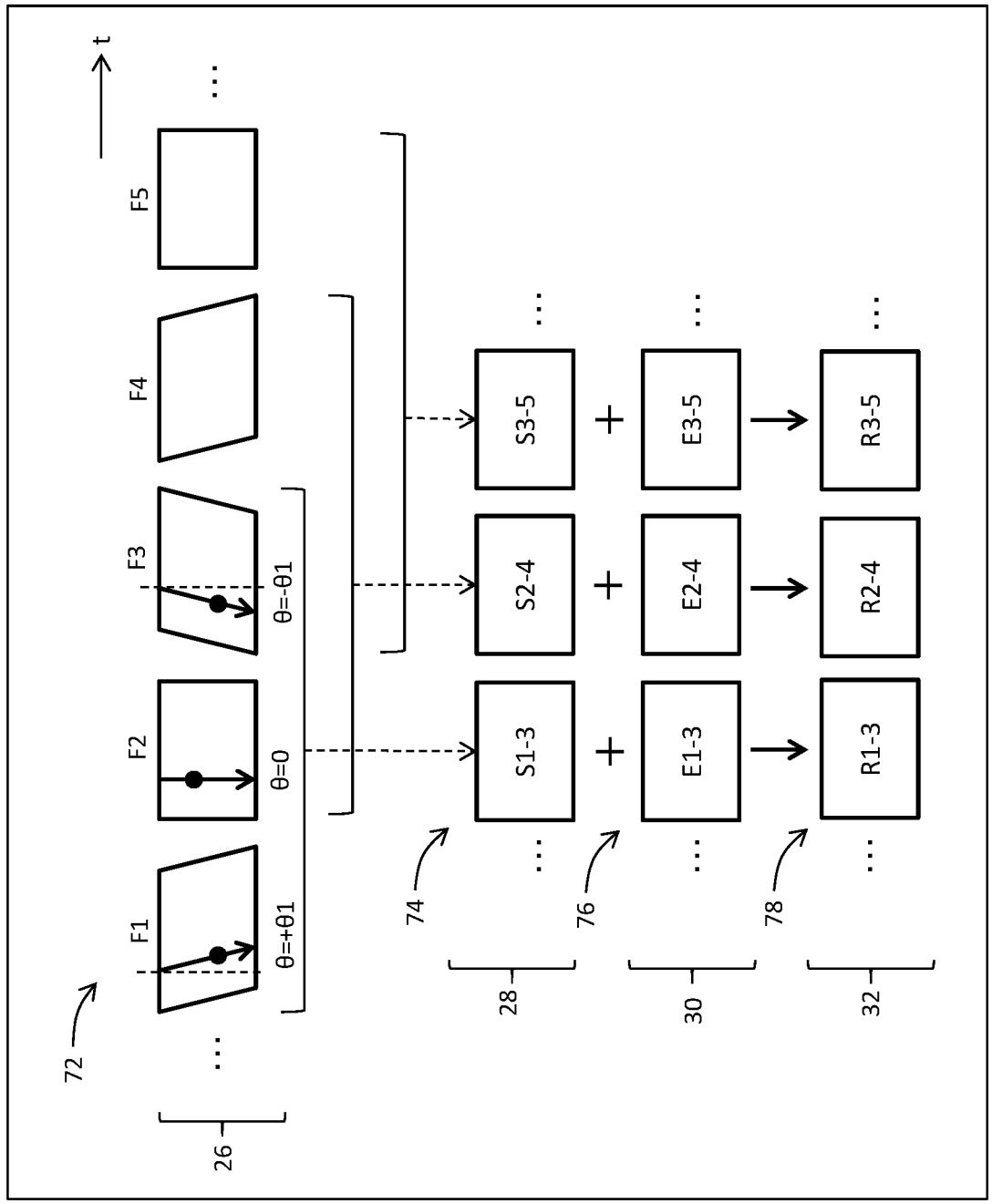
FIG. 5 schematically illustrates synthesizing processing according to a second embodiment.

FIG. 5 illustrates synthesizing processing according to the second embodiment. Elements in FIG. 5 that are similar to those illustrated in FIG. 2 are designated with the same reference numerals and will not be further described. The ultrasonic diagnostic apparatus according to the second embodiment has substantially the same configuration as the apparatus illustrated in FIG. 1, and different features will be described below.

In the second embodiment, spatial compounding is executed. Specifically, a first beam deflection angle is first set, then a second beam deflection angle is set, and subsequently a third beam deflection angle is set. Such a series of setting sequence is cyclically repeated, thereby generating a reception frame sequence 72. In the illustrated example, the first beam deflection angle is indicated as +θ1, the second beam deflection angle is indicated as 0, and the third beam deflection angle is indicated as −θ1.

In the illustrated example, a first transmission/reception condition for a long range, a transmission/reception condition for a close range, and a second transmission/reception condition for a long range together form one transmission/reception condition set, which is cyclically set. The first transmission/reception condition for a long range includes the first beam deflection angle +θ1, the transmission frequency f2, the transmission depth of focus d2, and the second reception pass band (BPF2). The transmission/reception condition for a close range includes the second beam deflection angle θ, the transmission frequency f1, the transmission depth of focus d1, and the first reception pass band (BPF1). Here, the relationships f1>f2 and d1<d2 are satisfied, and the first reception pass band (BPF1) is wider than the second reception pass band (BPF2). The second transmission/reception condition for a long range includes the third beam deflection angle −θ1, the transmission frequency f2, the transmission depth of focus d2, and the second reception pass band (BPF2).

The added frame generator 28 adds up three reception frames forming each reception frame set to generate an added frame for each reception frame set (see S1-3, S2-4, and S3-5). An added frame sequence 74 is thus generated from the reception frame sequence 72. The edge-enhanced frame generator 30 generates, for each reception frame set, an edge-enhanced frame (see E1-3, E2-4, and E3-5) from three reception frames forming each reception frame set. The maximum value method is applied to three transformed frames to generate one fused frame, which is then subjected to inverse transformation to form an edge-enhanced frame. An edge-enhanced frame sequence 76 is thus generated from the reception frame sequence 72.

The synthesizer 32 generates a synthesized frame sequence 78 (R1-3, R2-4 and R3-5) from the added frame sequence 74 and the edge-enhanced frame sequence 76. Here, the transmission frequency, the transmission depth of focus, and the reception pass band, for example, may be switched between the first transmission/reception condition for a long range and the second transmission/reception condition for a long range.

Figure 6:
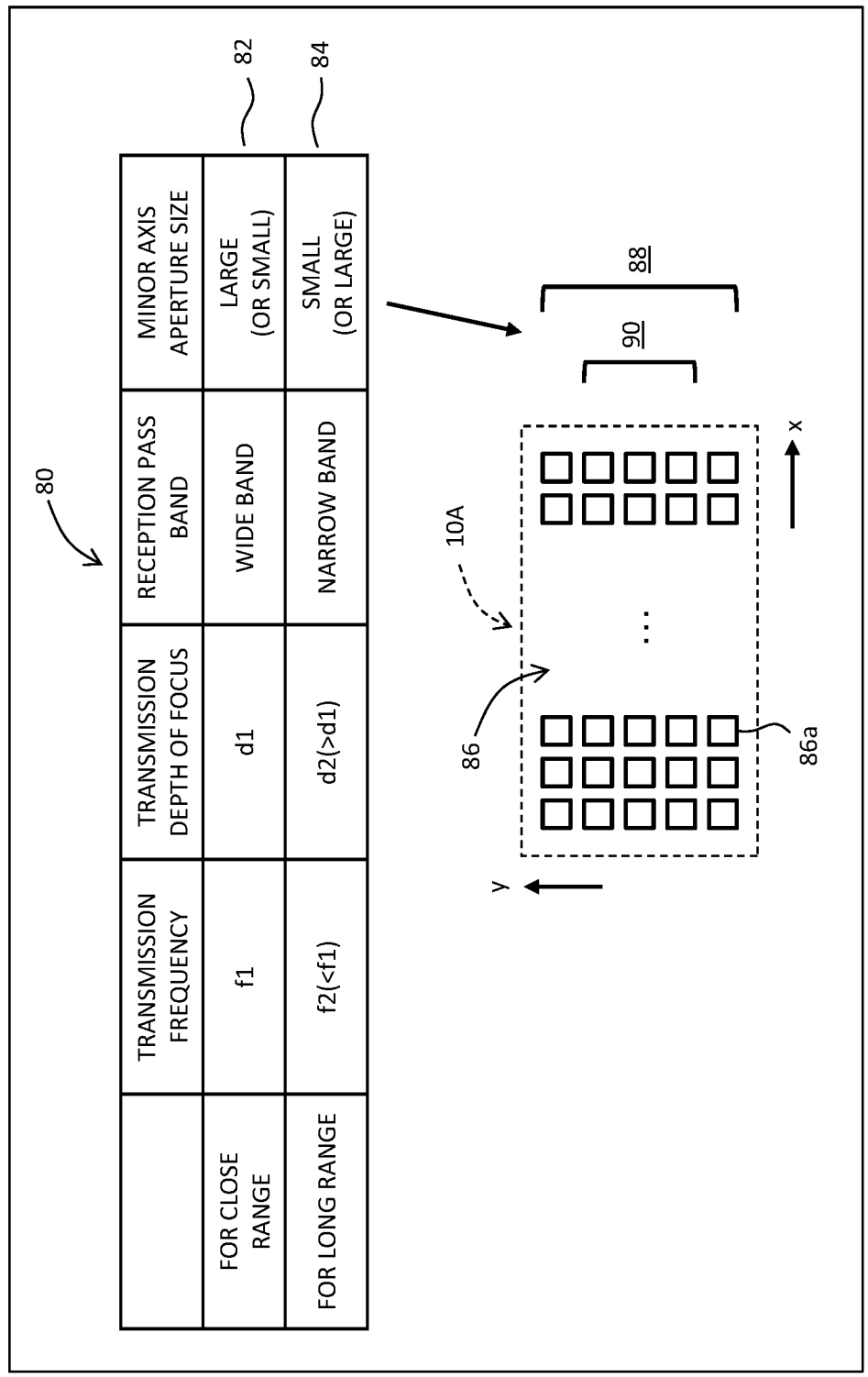
FIG. 6 schematically illustrates a third embodiment.

FIG. 6 illustrates a third embodiment. The ultrasonic diagnostic apparatus according to the third embodiment has a configuration similar to that of the apparatus illustrated in FIG. 1. A table 80 shows a first transmission/reception condition 82 for a close range and a second transmission/reception condition 84 for a long range. In the third embodiment, the aperture size in the minor axis direction (the sub direction which will be described below) is modified. More specifically, the first transmission/reception condition 82 for a close range includes a larger aperture size, and the second transmission/reception condition 84 for a long range includes a smaller aperture size.

FIG. 6 illustrates a probe according to the third embodiment with reference numeral 10A. The probe 10A includes a transducer array 86. The main direction of the electronic scanning direction is indicated as an x direction and the sub direction is indicated as a y direction. The transducer array 86 is composed of a plurality of transducers 86a arranged in the x and y directions.

The probe 10A in which the aperture is variable in the y direction in the transducer array 86 is referred to as a 1.25 D probe. The probe 10A capable of achieving variable aperture in the y direction and electronic focusing in the transducer array 86 is referred to as a 1.5 D probe. The probe 10A capable of variable aperture in the y direction, electronic focusing, and beam deflection within a predetermined angle range in the transducer array 86 is referred to as a 1.75 D probe.

In the third embodiment, the first transmission/reception condition 82 for a close range includes setting a large aperture (maximum aperture) 88 as the y-direction aperture in the transducer array 86, and the second transmission/reception condition 84 for a long range includes setting a small aperture 90 as the y-direction aperture in the transducer array 86.

Alternatively, the first transmission/reception condition 82 for a close range may include setting a small aperture as the y-direction aperture in the transducer array 86, and the second transmission/reception condition 84 for a long range may include setting a large aperture as the y-direction aperture in the transducer array 86.

Figure 7:
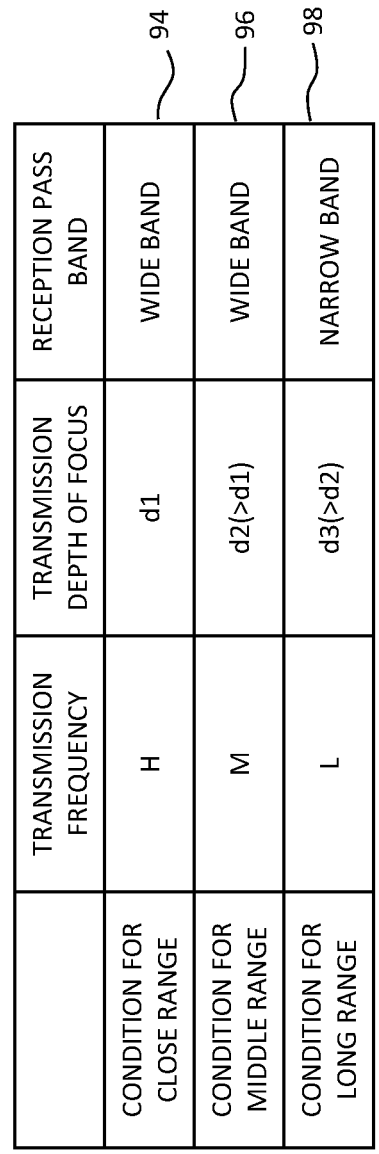
FIG. 7 illustrates a fourth embodiment.

FIG. 7 illustrates a fourth embodiment. The ultrasonic diagnostic apparatus according to the fourth embodiment has a configuration similar to that of the apparatus illustrated in FIG. 1. A table 92 shows a transmission/reception condition 94 for a close range, a transmission/reception condition 96 for a middle range, and a transmission/reception condition 98 for a long range. The transmission/reception condition 94 for a close range includes a high transmission frequency H, a transmission depth of focus d1, and a wide reception pass band. The transmission/reception condition 96 for a middle range includes a middle transmission frequency M, a transmission depth of focus d2, and a wide reception pass band. The transmission/reception condition 98 for a long range includes a low transmission frequency L, a transmission depth of focus d3, and a narrow pass band. Here, the relationships H>M>L and d1<d2<d3 are satisfied. The reception pass band refers to a reception pass band with a reception point at a predetermined depth.

In the above embodiments, in generating one synthesized frame from a plurality of reception frames, a greater weight may be applied to the most current reception frame. At this time, a plurality of weights to be applied to a plurality of reception frames may be varied in accordance with a correlation value calculated for each pair of frames. Here, a correlation value of phase information between the frames may be calculated.

The above techniques may be utilized for generating an ultrasound image including a puncture needle image. For example, a first transmission/reception condition for displaying a tissue more clearly and a second transmission/reception condition for displaying a puncture needle clearly may be cyclically set. At this time, the second transmission/reception condition may be set a greater number of times per unit time than the first transmission/reception condition.

The invention claimed is:

1. An ultrasonic diagnostic apparatus comprising: a generating unit configured to generate a frame sequence by repeating generation of transmitting signals and processing of received signals according to a plurality of transmission/reception conditions that are set cyclically; and a synthesizing unit configured to generate a synthesized frame sequence from the frame sequence, the synthesizing unit generating, for each frame set of frame sets in the frame sequence, a synthesized frame based on a plurality of frames forming the frame set, the synthesizing unit comprising a first synthesizing unit configured to generate a plurality of intermediate frames having different properties, based on the frame set, and a second synthesizing unit configured to synthesize the plurality of intermediate frames to generate the synthesized frame, wherein the plurality of transmission/reception conditions comprise a first transmission/reception condition for a close range and a second transmission/reception condition for a long range, the first transmission/reception condition includes a first transmission frequency and a first transmission depth of focus, and the second transmission/reception condition includes a second transmission frequency that is lower than the first transmission frequency and a second transmission depth of focus that is greater than the first transmission depth of focus, wherein the ultrasonic diagnostic apparatus further configured to calculate an evaluation value based on at least one of the plurality of intermediate frames, the plurality of intermediate frames including an added image and an edge-enhanced image; and wherein the ultrasonic diagnostic apparatus further comprising: a control unit configured to change, based on the evaluation value which corresponds to a difference between the added image and the edge-enhanced image, a combination of the first transmission frequency and the second transmission frequency; wherein the difference between the added frame and the edge-enhanced frame corresponds to the amount of edge and the combination of the plurality of transmission frequencies included in the plurality of transmission/reception conditions is changed to increase the amount of edge when the evaluation value is less than a threshold value.

2. The ultrasonic diagnostic apparatus according to claim 1, wherein the control unit is configured to set the first transmission depth of focus and the second transmission depth of focus based on a range of diagnostic depth.

3. The ultrasonic diagnostic apparatus according to claim 1, wherein
    the first transmission/reception condition includes a first reception pass band, and
    the second transmission/reception condition includes a second reception pass band that is narrower than the first reception pass band.

4. The ultrasonic diagnostic apparatus according to claim 1, wherein
    the first transmission/reception condition includes a first beam deflection angle, and
    the second transmission/reception condition includes a second beam deflection angle that is different from the first beam deflection angle.

5. The ultrasonic diagnostic apparatus according to claim 1, comprising:
    a transducer array comprising a plurality of transducers arranged along a main direction and a sub direction, wherein
    the first transmission/reception condition includes a first aperture size that is an aperture size in the sub direction, the second transmission/reception condition includes a second aperture size that is an aperture size in the sub direction, the second aperture size being different from the first aperture size.

6. The ultrasonic diagnostic apparatus according to claim 1, wherein the first synthesizing unit is configured to generate the added image and the edge-enhanced image as the plurality of intermediate frames, and the second synthesizing unit is configured to synthesize the added image and the edge-enhanced image to generate the synthesized frame.

7. A method of controlling an ultrasonic diagnostic apparatus, the method comprising: generating a frame sequence by repeating generation of transmitting signals and processing of received signals according to a plurality of transmission/reception conditions that are set cyclically; for each of frame sets in the frame sequence, generating a plurality of intermediate frames having different properties based on each frame set; for each of the frame sets, synthesizing the plurality of intermediate frames to generate a synthesized frame for forming an ultrasound image; calculating an evaluation value based on at least one of the plurality of intermediate frames, the plurality of intermediate frames including an added frame and an edge-enhanced frame; and changing, based on the evaluation value which corresponds to a difference between the added frame and the edge-enhanced frame, a combination of a plurality of transmission frequencies included in the plurality of transmission/reception conditions; wherein the difference between the added frame and the edge-enhanced frame corresponds to the amount of edge and the combination of the plurality of transmission frequencies included in the plurality of transmission/reception conditions is changed to increase the amount of edge when the evaluation value is less than a threshold value.

* * * * *